United States Patent [19]

Elefante

[11] Patent Number: 4,638,081
[45] Date of Patent: Jan. 20, 1987

[54] PROCESS FOR PREPARING α-ASPARTYL-L-PHENYLALANINE METHYL ESTER

[75] Inventor: Biagio Elefante, Gorgonzola, Italy

[73] Assignee: DE-BI Derivati Biologici International SpA, Milan, Italy

[21] Appl. No.: 608,983

[22] Filed: May 10, 1984

[30] Foreign Application Priority Data

May 13, 1983 [IT] Italy ................................ 21080 A/83

[51] Int. Cl.$^4$ ........................ C07C 101/32; C07K 5/06
[52] U.S. Cl. .................................. 560/40; 260/998.21; 530/801
[58] Field of Search .................... 260/112.5 R, 998.21; 560/40; 530/801

[56] References Cited

U.S. PATENT DOCUMENTS

| | | | |
|---|---|---|---|
| 3,786,039 | 1/1974 | Ariyoski et al. | 260/112.5 R |
| 4,309,341 | 1/1982 | Kubo et al. | 260/112.5 R |
| 4,543,349 | 9/1985 | Callahan et al. | 514/11 |

OTHER PUBLICATIONS

Derwent Abst., 87762x/47, Mar. 28, 1975, J5 1113-841.
Yasutake et al, Bull. Chem. Soc. Jpn. 50 (9), 2413–2416 (1977).
Pavlova, Russian Chem. Rev. 50 (4), 316–323 (1981).
Chemical Abstracts, Yasutake et al., 88:23368g, referring to Bull. Chem. Soc. Jpn. 50(9), 2413–2416(1977).

*Primary Examiner*—Delbert R. Phillips
*Attorney, Agent, or Firm*—Hedman, Gibson, Costigan & Hoare

[57] ABSTRACT

A process for preparing α-L-aspartyl-L-phenylalanine methyl ester consisting of:

bringing N-formyl-L-aspartic anhydride and L-phenylalanine methyl ester, in a molar ratio equal or approximately equal to 1:1, into contact with a solid cation exchange resin having free sulphonic, phosphonic or carboxylic acid groups, the ration of the acid equivalents of said resin acid groups to the number of moles of the one or other reagent being equal to or less than about 1:1, and operating in the liquid phase in an inert organic solvent at a temperature of about 40° C. or less, until a mixture of N-formyl-α-L-aspartyl-L-phenylalanine methyl ester and N-formyl-β-L-aspartyl-L-phenylalanine methyl ester forms in which the α isomer prevails over the β isomer;

deformylating said N-formyl-α-L-aspartyl-L-phenylalanine methyl ester and N-formyl-β-L-aspartyl-L-phenylalanine methyl ester; and separating and recovering the α-L-aspartyl-L-phenylalanine methyl ester from said deformylated products.

11 Claims, No Drawings

PROCESS FOR PREPARING α-ASPARTYL-L-PHENYLALANINE METHYL ESTER

BACKGROUND OF THE INVENTION

1. Field of the Invention

This invention relates to a process for preparing 6o-L-aspartyl-L-phenylalanine methyl ester, which is used as a sweetening agent.

2. Description of the Prior Art

Belgian Pat. No. 717,373 describes the sweetening characteristics, in particular for dietetic purposes, of the lower alkyl esters of 6o-L-aspartyl-L-phenylalanine:

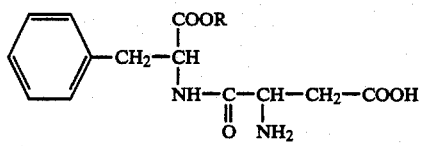

Of these compounds, 6o-L-aspartyl-L-phenylalanine methyl ester (where R is —CH$_3$ in the preceding formula (I)), also known as 6o-aspartame, is assuming particular commercial importance. In a known process of the art, the compounds (I) are obtained by a method which comprises reacting a lower alkyl eter of phenylalanine with an aspartic acid derivative in which the amino function is protected by a benzyloxycarbonyl group, and the β-carboxy function by a benzyl ester group, the 6o-carboxy group having previously been transformed into an ester function by rection with p-nitrophenol. The protector groups are then eliminated from the reaction product obtained in this manner. This process is complicated because of the many operations which are required, the use of numerous raw materials, and the mediocre overall yields, which makes the process uneconomical and little suitable for application on a commercial scale.

In French Pat. No. 7015787, the compounds of formula (I) are obtained by a process which comprises reacting L-aspartic anhydride, protected at the nitrogen by a formyl, carbobenzoxy or para-methoxycarbobenzoxy protector group, with a lower alkyl ester of L-phenylalanine, operating in an organic solvent. The nitrogen protector group is then eliminated from the reaction product obtained in this manner.

In published Japanese patent application Ser. No. 113,841/76 of 7.10.1976, a lower alkyl ester of N-formyl-6o-L-aspartyl-L-phenylalanine is prepared by reacting a lower alkyl ester of L-phenylalanine with N-formyl-L-aspartic anhydride, operating in the presence of an organic acid having a dissociation constant of less than $10^{-4}$ at 25° C. The reaction product obtained in this manner can then be treated for deformylation. In addition to giving the α isomer (preceding formula (I)), these known processes also give rise to the formation of rather large quantities of the β isomer:

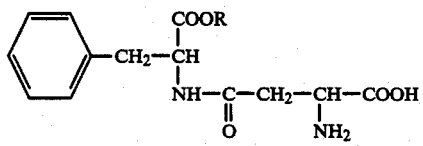

the presence of which is undesirable. In this respect, it has been found that only the α isomer, and in particular the methyl derivative of said isomer (where R is —CH$_3$ in the preceding formula (I)), has a sweetening power analogous to that of natural sugar and free from secondary tastes, whereas the methyl derivative of the β isomer (where R is —CH$_3$ in the preceding formula (II)) has a slightly bitter taste. A technical problem which arises in the processes under discussion is therefore to direct the reaction towards the prevalent formation of the α isomer.

However, when operating by the process of the aforesaid French patent, there is on the one hand poor reaction selectivity towards the formation of the α isomer, and on the other hand difficulty in controlling the ratio of the α to the β isomer in the reaction products. In this respect, said ratio is strongly influenced by various factors such as the chosen solvent and the nature of the protective groups in that reaction stage in which the L-phenylalanine alkyl ester is reacted with L-aspartic anhydride protected at the nitrogen. The result is that said process is hardly attractive and of little interest for commercial application. When operating by the process of the aforesaid Japanese patent application, it is possible to control the reaction to a certain extent towards the prevalent formation of the α isomer. It has, however, been found that these more advantageous results in terms of selectivity towards the α isomer are obtained if large quantities of organic acid are present. This makes the process costly, and its operation is complicated particularly in the separation and recovery of the useful reaction products.

SUMMARY OF THE INVENTION

The object of the present invention is therefore a process for preparing α-L-aspartyl-L-phenylalanine methyl ester which is free or substantially free of the aforesaid drawbacks. In particular the object of the present invention is a process which enables the reaction to be reliably controlled towards the formation of the α isomer of said L-aspartyl-L-phenylalanine methyl ester while operating in a simple and ecomonically convenient manner. The present invention is based essentially on the unexpected observation that the progress of the reaction between L-phenylalanine methyl ester and N-formyl-L-aspartic anydride is influenced both by the presence of a solid cation exchange resin having free acid groups, and by the concentration of said resin, in the sense that the reaction yield and the selectivity towards the α isomer in the reaction product increase, within a certain range, as the ratio of the acid equivalents of said resin acid groups to the moles of said reagents decreases.

Description of the Invention

In accordance therewith, α-L-aspartyl-L-phenylalanine methyl ester is prepared according to the invention by a process consisting of:

bringing N-formyl-L-aspartic anhydride and L-phenylalanine methyl ester, in a molar ratio equal or approximately equal to 1:1, into contact with a solid cation exchange resin having free sulphonic, phosphonic or carboxylic acid groups, the ratio of the acid equivalents of said resin acid groups to the number of moles of the one or other reagent being equal to or less than about 1:1, and operating in the liquid phase in an inert organic solvent at a temperature of about 40° C. or less, until a mixture of N-formyl-α-L-aspartyl-L- phenylalanine methyl ester and N-formyl-β-L-aspartyl-L-phenylalanine methyl ester forms in which the molar ratio of the α isomer to the β isomer depends on the chosen ratio of the resin acid equivalents to the number of moles of reagents;

deformylating said N-formyl-α-L-aspartyl-L-phenylalanine methyl ester and N-formyl-β-L-aspartyl-L-phenylalanine methyl ester; and separating and recovering the α-L-aspartyl-L-phenylalanine methyl ester from said deformylated products.

According to the process of the present invention, N-formyl-L-aspartic anhydride and L-phenylalanyl methyl ester are brought into contact in a molar ratio equal or approximately equal to 1:1, and are reacted in the presence of a solid cation exchange resin having free sulphonic, phosphonic or carboxylic acid groups, to give a mixture of α and β isomers of N-formyl-L-aspartyl-L-phenylalanine methyl ester. Cation exchange resins suitable for the purpose are those with sulphonic groups on a polystyrene base, a base of polystyrene cross-linked with divinylbenzene, and a phenolic base.

Also useful for the purpose are cation exchange resins having phosphonic groups on a polystyrene or cross-linked polystyrene base, and those having carboxyl groups on a methacrylic base.

Examples of commercial resins usable in the process of the present invention are those known as DOWEX 50 W of the Dow Chemical Company, and AMBERLITE IR C50 and AMBERLITE IR 120 of the Rohn & Hass Company.

These resins, which are used in free acid form, generally have an exchange capacity of between about 4 and about 10 meq per gram of dry resin.

According to the process of the present invention, the resin quantity used is such as to provide between 0.05 and approximately 1 acid equivalent for each mole of the one or of the other reagent fed into the reaction environment.

Resin quantities which provide less than 0.05 acid equivalents do not exert sufficient action on the reaction, whereas quantities exceeding 1 acid equivalent are undesirable because of the low yield and low selectivity towards the formation of the α isomer. In this second circumstance there are also difficulties in crystallizing the reaction products. The preferred values of the ratio under discussion are those between 0.05 and 0.5, and the absolutely preferred value is equal to or in the order of 0.1, in that it provides the best conditions in terms of reaction yield and selectivity towards the formation of the α isomer.

According to the present invention, the reaction between N-formyl-L-aspartic anhydride and L-phenylalanine methyl ester is carried out in the liquid phase in an inert (non-reactive) organic solvent. The solvents suitable for the purpose are generally chosen from those alkyl esters, aliphatic ketones and chlorinated aliphatic hydrocarbons which are liquid at the temperature at which the reaction is carried out. Specific examples of solvents of the aforesaid classes are ethyl acetate, acetone and chloroform. The choice of solvent is not particularly critical because the influence of the solvent on the distribution of the α and β isomers in the reaction products is low in the process of the present invention. The temperature at which the reaction between N-formyl-L-aspartic anhydride and L-phenylalanyl methyl ester is conducted can generally vary from about −15 to about 40° C., and the corresponding reaction time varies from about 2 hours to about 5 minutes.

In practice it is convenient to operate at ambient temperature (20-25° C.) or close to ambient temperature. In this case, the time required in order to complete or substantially complete the reaction is of the order of 8-10 minutes.

When operating under the aforesaid general conditions, a conversion of the reagents into the α and β isomers of N-formyl-L-aspartyl-L-phenylalanine methyl ester as reaction products is typically between 70% and 90%, with a ratio of α isomer to β isomer generally varying between 75:25 and 85:15.

When operating under the aforesaid preferred conditions, the conversion values are of the order of 85-90% and the ratio of α isomer to β isomer between 80:20 and 85:15.

Consequently the cation exchange resins carrying free acid groups are able to exert their effect even when used in catalytic quantities, favoring in such a circumstance the formation of the α isomer rather than the β isomer. This behavior was completely unpredictable because in the reaction under discussion the use of an organic acid such as acetic acid leads to a reduction in the selectivity towards the α isomer, to pass from an acid quantity equal to the equimolar quantity with respect to one or other of the reagents, to a quantity less than the equimolar quantity.

In practice, in preparing the α and β isomers of N-formyl-L-aspartyl-L-phenylalanyl methyl ester, the reaction can be conducted discontinuously, with the cation exchange resin in the form of granules suspended in the liquid reaction medium, while maintaining the sustem under effective agitation. Alternatively, the cation exchange resin can be kept in a fixed position in the reaction vessel, for example between porous baffles, and ensuring its contact with the reagents by agitation or circulation of the liquid medium. According to one embodiment, a "reaction foot" is prepared containing the cation exchange resin and the chosen solvent in which the N-formyl-L-aspartic anhydride is dissolved or suspended. The L-phenylalanine methyl ester dissolved in the same solvent is added to this reaction foot.

According to a further embodiment, the reagents in the relative solvent are fed continuously to one end of a reactor containing the cation exchange resin in the form of a fixed bed. In this case, the reaction mixture is recovered continuously at the other end of the reactor.

In all cases, at the end of the reaction the cation exchange resin and the solvent are removed from the reaction mixture, the former for example by filtration and the latter generally by evaporation, and the residual mixture is subjected to deformylation treatment in order to obtain the α and β isomers of L-aspartyl-L-phenylalanyl methyl ester.

Any known deformylation process can be used for this purpose. However, according to a preferred embodiment, normal hydrochloric acid in a hydroalcoholic solution, in particular hydromethanolic, is used with a water:alcohol weight ratio of the order 1:6.5, under boiling conditions. On operating in this manner, complete or substantially complete deformylation is attained in a short time of the order of 0.5 hours.

The reaction mixture thus obtained is neutralized, for example by treatment with sodium carbonate, and the alcohol is removed by evaporation. Finally, the required product in the form of α-L-aspartyl-L- phenylalanine methyl ester is separated by crystallization from aqueous solution.

The process according to the present invention in particular has the advantage of high yield and high selectivity in terms of the required reaction product. In addition, said process is simple overall, economically convenient and therefore suitable for implementing on a commercial scale.

Thus, for example, the use of the cation exchange resin, which can be easily separated and extracted from the reaction medium, enables the reaction involved in forming and α and β isomers of the N-formyl-L-aspartyl-L-phenylalanine methyl ester, the reaction involved in deformylating said isomers, and the crystallization of the final required product, namely α-L-aspartyl-L-phenylalanine methyl ester, to be carried out in the same reactor.

The experimental examples given hereinafter illustrate but do not limit the invention. Examples 1 to 12 are conducted according to the invention, and the other examples are for comparison purposes.

EXAMPLE 1

A solution of L-phenylalanine methyl ester in ethyl acetate is prepared by dissolving 11 g (0.05 moles) of L-phenylalanine methyl ester hydrochloride in 50 ml of water and then adding 6 g of $K_2CO_3$. The aqueous solution thus obtained is extracted twice, each time with 100 ml of ethyl acetate. The organic layers obtained in this manner are added together, dried over anhydrous $Na_2SO_4$, and concentrated under reduced pressure to a final volume of 50 ml. 30 ml of ethyl adetate, 7.2 g (0.05 moles) of N-formyl-L-aspartic anhydride and 1.0 g of the commercial cation exchange resin DOWEX 50 W (of the Dow Chemical Company), previously dried at 50° C. under vacuum to constant weight, are fed into a reaction flask of 500 ml capacity, fitted with an agitator and dropping funnel.

The resin used carries sulphonic acid groups on a polystyrene matrix and has an exchange capacity of 5 meq. per gram of dry resin. Consequently the ratio of the acid equivalents of the resin acid groups to the moles of N-formyl-L-aspartic anhydride is 0.1. The mass is agitated in the flask to obtain a suspension. The solution of L-phenylalanine methyl ester in ethyl acetate is added to this agitated suspension by means of the dropping funnel over a time of about 8 minutes, while maintaining the temperature of the mass at about 25° C. At the end of this time a solution is obtained from which the cation exchange resin is separated by filtration. The solution is then cooled to 0° C. and a crystalline precipitate is obtained constituted by a mixture of the α and β isomers of N-formyl-L-aspartyl-L-phenylalanine methyl ester (14.1 g, yield 87%). This precipitate is subjected to HPLC analysis in order to check the ratio of the α to the β by comparison with known samples. The HPLC determinations are carried out using a Perkin-Elmer chromatograph, series 3, with a 7 micron RP8 column, 250×4 mm; eluent used: continuous gradient between solvents: (A) 65 parts of monobasic potassium phosphate 0.07 molar at pH 4+35 parts of methanol; and (B) 65 parts of water +35 parts of methanol; flow rate 1 ml per minute.

Detector: Perkin-Elmer spectrophotometer LC-55B at 210 mu.

The analysis showed an α isomer:β isomer ratio of 82:18.

EXAMPLE 2

The procedure of Example 1 is repeated, but using 10 g of DOWEX 50 cation exchange resin. In this manner the ratio of the acid equivalents of the resin acid groups to the moles of N-formyl-L-aspartic anhydride fed is equal to 1.

12.5 g (yield 77.5%) of crystalline product are obtained consisting of a mixture of α and β isomers of N-formyl-L-aspartyl-L-phenylalanine methyl ester, in which the ratio of the α isomer to the β isomer is 70:30.

EXAMPLE 3

The procedure of Example 1 is repeated, but using 1.16 g of the commercial cation exchange resin AMBERLITE IT 120 (of the Rohm & Hass Company), which had been previously dried at 50° C. under vacuum to constant weight.

The resin used carries sulphonic acid groups on a matrix of polystyrene cross-linked with divinylbenzene and has an exchange capacity of 4.3 meq. per gram of dry resin.

In this manner the ratio of the acid equivalents of the resin acid groups to the moles of N-formyl-L-aspartic anhydride fed is equal to 0.01.

14.1 g (yield 87%) of crystalline product are obtained consisting of the α and β isomers of N-formyl-L-aspartyl-L-phenylalanine methyl ester, in which the ratio of the α isomer to the β isomer is 85:15.

EXAMPLE 4

The procedure of Example 3 is repeated, but using 11.6 g of the commercial cation resin AMBERLITE IR 120. In this manner, the ratio of the acid equivalents of the resin acid groups to the moles of N-formyl-L-aspartic anhydride fed is equal to 1.

11.3 g (yield 70%) of crystalline product are obtained, consisting of the α and β isomers of N-formyl-L-aspartyl-L-phenylalanine methyl ester, in which the ratio of the α isomer to the β isomer is 75:25.

EXAMPLE 5

The procedure of Example 1 is followed, but using 500 mg of the commercial cation exchange resin AMBERLITE IR C 50 (of the Rohm & Hass Company), previously dried at 50° C. under vacuum to constant weight.

The resin used carries carboxylic acid groups on a methacrylic matrix and has an exchange capacity of 10 meq. per gram of dry resin. In this manner, the ratio of the acid equivalents of the resin acid groups to the moles of N-formyl-L-aspartic anhydride fed is equal to 0.1.

14.5 g (yield 90%) of crystalline product are obtained, consisting of the α and β isomers of N-formyl-L-aspartyl-L-phenylalanine methyl ester, in which the ratio of the α isomer to the β isomer is 80:20.

EXAMPLE 6

The procedure of example 5 is repeated, but using 5 g of the commercial cation exchange resin AMBERLITE IR C50. In this manner, the ratio of the acid equivalents of the resin acid groups to the moles of N-formyl-L-aspartic anhydride is equal to 1.

12.9 g (yield 80%) of crystalline product are obtained, consisting of the α and β isomers of N-formyl-L-aspartyl-L-phenylalanine methyl ester, in which the ratio of the α isomer to the β isomer is 75:25.

EXAMPLES 7 AND 8

The procedure of example 1 is repeated, but using 0.8 g and 0.93 g of the commercial cation exchange resins DOWEX 50 W and AMBERLITE IR 120 respectively. In this manner, the ratio of the acid equivalents of the resin acid groups to the moles of N-formyl-L-aspartic anhydride fed is 0.08.

In the first case, a crystalline precipitate of the α and β isomers of N-formyl-L-aspartyl-L-phenylalanine methyl ester is obtained with a yield of 82%, and in which the ratio of the α isomer to the β isomer is 80:20.

In the second case, a crystalline precipitate of said isomers is obtained with a yield of 86%, and which the ratio of the α isomer to the β isomer is 85:15.

EXAMPLES 9 AND 10

The procedure of the two Examples 7 and 8 is repeated, but using 1.3 g and 1.51 g of the commercial cation exchange resins DOWEX 50 W and AMBERLITE IR 120 respectively.

In this manner the ratio of the acid equivalents of the resin acid groups to the moles of N-formyl-L-aspartic anydride fed is 0.13. In the first case, a crystalline precipitate of the α and β isomers of N-formyl-L-aspartyl-L-phenylalanine methyl ester is obtained with a yield of 82%, and in which the ratio of the α isomer to the β isomer is 75:25.

In the second case a crystalline precipitate of said isomers is obtained with a yield of 84%, and in which the ratio of the α isomer to the β isomer is 83:17.

EXAMPLE 11

The procedure of Example 5 is repeated, but using 650 mg of the commercial cation exchange resin AMBERLITE IR C 50.

In this manner, the ratio of the acid equivalents of the resin acid groups to the moles of N-formyl-L-aspartic anhydride fed is 0.13. A crystalline precipitate of the α and β isomers of N-formyl-L-aspartyl-L-phenylalanine methyl ester is obtained with a yield of 85%, in which the ratio of the α isomer to the β isomer is 80:20.

EXAMPLE 12

The procedure of Example 1 is repeated, and after separating the resin, the rection mixture is freed of the ethyl acetate solvent by boiling it off.

Normal hydrochloric acid in a hydromethanol solution in which the water:methanol weight ratio is 1:6.5, is added to the distillation residue. The mass is kept boiling for 30 minutes and at the end of this period is cooled and neutralized by adding sodium bicarbonate. The methanol is then evaporated, the solid precipitated by cooling to 0° C., and the precipitated solid crystallized from water to obtain the α-L-aspartyl-L-phenylalanine methyl ester, having a melting point of 245°–247° C., and a $[\alpha]_D^{20}$ of +30 (C=1, acetic acid).

EXAMPLE 13 (comparison)

The procedure of Example 1 is repeated, but without adding the ion exchange resin to the reaction mixture. On adding the L-phenylalanine methyl ester solution over a period of 10 minutes, 14 g (yield 87%) of the precipitate comprising the α and β isomers of N-formyl-L-aspartyl-L-phenylalanine methyl ester are obtained, in which the ratio of the α isomer to the β isomer is 57:43.

EXAMPLE 14 (comparison)

The procedure of Example 1 is repeated, but using 3 ml of glacial acetic in place of the ion exchange resin. In this manner, the molar ratio of the acetic acid to the fed N-formyl-L-aspartic anhydride is equal to 1.

14 g (yield 87%) of the precipitate comprising the α and β isomers of N-formyl-L-aspartyl-L-phenylalanine methyl ester are obtained, in which the ratio of the α isomer to the β isomer is 72:24.

EXAMPLE 15 (comparison)

The procedure of the preceding example is repeated, but feeding 1.5 ml of glacial acetic acid.

In this manner the molar ratio of the acetic acid to the fed N-formyl-L-aspartic anhydride is 0.5.

A precipitate comprising the α and β isomers of N-formyl-L-aspartyl-L-phenylalanine methyl ether is obtained with a yield of 80%, in which the ratio of the α isomer to the β isomer is 60:40.

EXAMPLE 16 (comparison)

The procedure of Example 1 is repeated but using 3.43 ml of acrylic acid in place of the ion exchange resin. In this manner the molar ratio of the acrylic acid to the fed N-formyl-L-aspartic anhydride is equal to 1.

12.7 g (yield 79%) of the precipitate comprising the α and β isomers of N-formyl-L-aspartyl-L-phenylalanine methyl ester are obtained, in which the ratio of the α isomer to the β isomer is 75:25.

What is claimed is:

1. A process for preparing α-aspartyl-L-phenylalanine methyl ester from N-formyl-L-aspartic anhydride and L-phenylalanine methyl ester, while simultaneously increasing the relative production of the α isomer over the β isomer, comprising:
   (a) contacting N-formyl-L-aspartic anhydride and L-phenylalanine methyl eter, in a molar ratio of about 1:1, with a solid cation exchange resin having free sulphonic, phosphonic or carboxylic acid groups, the ratio of the acid equivalents of said resin acid groups to the number of moles of the one or the other of said reagents being from about 0.05:1 to about 1:1, and operating in the liquid phase in an inert organic solvent at a temperature of about −15° C. to about 40° C. for a period of about 5 minutes to about 2 hours, until a mixture of N-formyl-α-L-aspartyl-L-phenylalanine methyl ester and N-formyl-β-L-aspartyl-L-phenylalanine methyl ester forms;
   (b) deformylating said N-formyl-α-L-aspartyl-L-phenylalanine methyl ester and N-formyl-β-L-aspartyl-L-phenylalanine methyl ester; and
   (c) separating and recovering the α-L-aspartyl-L-phenylalanine methyl ester from said deformylated products.

2. A process as claimed in claim 1, wherein in stage (a) the cation exchange resins are chosen from those having sulphonic groups on a polystyrene base, on a base of polystyrene cross-linked with divinylbenzene or on a phenolic base, or those having phosphonic groups on a polystyrene or cross-linked polystyrene base, or those having carboxyl groups on a methacrylic base.

3. A process as claimed in claim 1, wherein said ratio of acid equivalents of the cation exchange resin acid groups to the number of moles of the one or the other reagent is between 0.05:1 and 0.5:1.

4. A process as claimed in claim 1, wherein said ratio of acid equivalents of the cation exchange resin acid groups to the number of moles of the one or the other reagent is equal to or in the order of 0.1:1.

5. A process as claimed in claim 1, wherein in stage (a) the process is conducted in the presence of an organic solvent chosen from alkyl esters, aliphatic ketones and chlorinated aliphatic hydrocarbons.

6. A process as claimed in claim 5, wherein said solvent is chosen from methyl acetate, acetone and chloroform.

7. A process as claimed in claim 6, which is conducted at ambient temperature (20°-25° C.) with a contact time of 8-10 minutes.

8. A process as claimed in claim 1, wherein stage (b) is conducted on the reaction mixture originating from stage (a) and from which the resin and solvent have been removed, by heating to the boiling point in an aqueous-methanolic hydrochloric acid environment.

9. A process as claimed in claim 8, wherein in said stage (b) the process is carried out with normal hydrochloric acid in a water-methanol solution having a water:methanol weight ratio of 1:6.5, under boiling conditions, for a period of time of 0.5 hours.

10. A process as claimed in claim 1, wherein stage (c) is conducted by crystallization from an aqueous solution.

11. A process for preparing α-L-aspartyl-L-phenylalanine methyl ester from N-formyl-L-aspartic anhydride and L-phenylalanine methyl ester, while simultaneously increasing the relative production of the α isomer over the β isomer, comprising:

(a) contacting substantially equimolar amounts of N-formyl-L-aspartic anhydride and L-phenyl-alanine methyl ester in an inert organic solvent selected from alkyl esters, aliphatic ketones or chlorinated aliphatic hydrocarbons in the presence of a solid cation exchange resin having free sulphonic, phosphonic or carboxylic acid groups on a polystyrene, a cross-linked polystyrene, a polystyrene cross-linked with divinylbenzene, a phenolic, or a methacrylic base having an exchange capacity of between about 4 and about 10 meq per gram of dry resin, wherein the ratio of the acid equivalents of said cation exchange resin acid groups to the number of moles of one or the other of said reagents is about 0.05:1 to about 1:1, at a temperature of about $-15°$ C. to about 40° C. for a period of about 5 minutes to about 2 hours, until a mixture of N-formyl-α-L-aspartyl-L-phenylalanine methyl ester and N-formyl-β-L-aspartyl-L-phenylalanine methyl ester forms;

(b) removing the cation exchange resin by filtration and removing the organic solvent by evaporation;

(c) deformylating said N-formyl-α-L-aspartyl-L-phenylalanine methyl ester and N-formyl-β-L-aspartyl-L-phenylalanine methyl ester by boiling in a solution of normal hydrochloric acid in acqueous methanol for a period of about 0.5 hour; and (d) recovering the α-L-aspartyl-L-phenylalanine methyl ester from the deformylated products by crystallization.

* * * * *